United States Patent
Santi et al.

(10) Patent No.: US 10,543,216 B2
(45) Date of Patent: Jan. 28, 2020

(54) MODUS OF ADMINISTRATION OF IRON, AND NEW FORMULATIONS ADAPTED FOR THE SAID GOAL

(71) Applicant: BIOFER S.P.A., Medolla (IT)

(72) Inventors: Patrizia Santi, Salsomaggiore Terme (IT); Dario Bosi, Reggiolo (IT); Alessandro Lapini Sacchetti, Modena (IT); Egidio Marchi, Casalecchio di Reno (IT); Cristina Padula, Parma (IT)

(73) Assignee: BIOFER S.P.A., Medolla (IT)

( * ) Notice: Subject to any disclaimer, the term of this patent is extended or adjusted under 35 U.S.C. 154(b) by 0 days.

(21) Appl. No.: 14/903,814

(22) PCT Filed: Jul. 9, 2014

(86) PCT No.: PCT/IB2014/001303
§ 371 (c)(1),
(2) Date: Jan. 8, 2016

(87) PCT Pub. No.: WO2015/004519
PCT Pub. Date: Jan. 15, 2015

(65) Prior Publication Data
US 2016/0151384 A1 Jun. 2, 2016

(30) Foreign Application Priority Data
Jul. 9, 2013 (IT) .............................. MI2013A1147

(51) Int. Cl.
*A61K 31/555* (2006.01)
*A61K 9/00* (2006.01)
(Continued)

(52) U.S. Cl.
CPC ............ *A61K 31/555* (2013.01); *A61K 9/006* (2013.01); *A61K 9/0056* (2013.01); *A61K 31/519* (2013.01); *A61K 33/26* (2013.01)

(58) Field of Classification Search
None
See application file for complete search history.

(56) References Cited

U.S. PATENT DOCUMENTS 4,058,621 A   11/1977  Hill
4,058,624 A   11/1977  Jacobus et al.
(Continued)

FOREIGN PATENT DOCUMENTS

CN   102065686 A   5/2011
JP       6284023 A   4/1987
(Continued)

OTHER PUBLICATIONS

[Online]; [Retrieved on Jan. 15, 2016] Retrieved from the internet at http://www.bloodjournal.org; Kurt R. Reissmann, et al., "Acute Intestinal Iron Intoxication: II. Metabolic, Respiratory and Circulatory Effects of Absorbed Iron Salts," American Society of Hematology: Blood Journal, 1955, pp. 46-51, vol. 10.
(Continued)

*Primary Examiner* — Bethany P Barham
*Assistant Examiner* — Barbara S Frazier
(74) *Attorney, Agent, or Firm* — Cantor Colburn LLP (57) ABSTRACT

A new modus and a new regimen of administration of divalent iron relates to therapy of hyposideremia, at the same time reducing toxic side effects. New formulations containing divalent iron compounds are adapted to release iron for intrabuccal absorption, preferably by sublingual absorption, that achieve these objects.

19 Claims, 4 Drawing Sheets

(51) Int. Cl.
    A61K 31/519    (2006.01)
    A61K 33/26     (2006.01)

(56) References Cited

U.S. PATENT DOCUMENTS

| | | | |
|---|---|---|---|
| 2003/0082107 A1 | 5/2003 | Dugger | |
| 2003/0104078 A1* | 6/2003 | Barrett-Reis | A23L 33/15 424/727 |
| 2005/0063918 A1 | 3/2005 | Charmot et al. | |
| 2007/0065521 A1* | 3/2007 | Venkataraman | A61K 31/555 424/646 |
| 2012/0177700 A1* | 7/2012 | Imran | A61K 9/14 424/400 |
| 2016/0296463 A1* | 10/2016 | Chin | A61K 31/485 |

FOREIGN PATENT DOCUMENTS

| | | |
|---|---|---|
| JP | 2009533388 A | 9/2009 |
| KZ | 581 C1 | 8/2003 |
| WO | 2009143097 A1 | 11/2009 |

OTHER PUBLICATIONS

[Online]; [Retrieved on Jan. 15, 2016]; Retrieved from the internet at http://www.bloodjournal.org; Kurt R. Reissmann et al., "Acute Intestinal Iron Intoxication: I. Iron Absorption, Serum Iron and Autopsy Findings," American Society of Hematology: Blood Journal, 1955, pp. 35-45, vol. 10.
[Online]; [Retrieved on Jan. 15, 2016]; Retrieved from the internet http://www.jbc.org; Enst S. Henle, et al., "Formation, Prevention, and Repair of DNA Damage by Iron/Hydrogen Peroxide," The Journal of Biological Chemistry, Aug. 1997, pp. 19095-19098, vol. 272, No. 31.
[Online]; Retrieved from the Internet at http://www.aafp.org/afp; Shersten Killip, et al., "Iron Deficiency Anemia," American Family Physician, Mar. 2007, pp. 1-8, vol. 75, No. 5.
[Online]; Retrieved from the Internet at http://www.interscience.wile.com; Isabel Diaz Del Consuelo, et al., "Evaluation of Pig Esophageal Mucosa as a Permeability Barrier Model for Buccal Tissue," Journal of Pharmaceutical Sciences, Apr. 2005, pp. 2777-2788, vol. 94.
[Online]; Retrieved from the Internet at http://www.intl.elsevierhealth.com/journals/arob; Isabel Diaz Del Consuelo, et al., "Comparison of the Lipid Composition of Porcine Buccal and Esophageal Permeability Barriers," Archives of Oral Biology, Apr. 2005, pp. 981-987, vol. 50.
C. L. Witzleben, et al., "Iron Overload Heptotoxicity: A Postulated Pathogenesis," Clinical Toxicology, Dec. 1971, pp. 579-583, vol. 4.
Earl R. Stadtman, et al., "Reactive Oxygen-Mediated Protein Oxidation in Aging and Disease," American Chemical Society: Chemical Research Toxicology, 1997, pp. 485-494, vol. 10 No. 5.
H. E. Macdermot, "Editorial: Acute Iron Poisoning in Children," The Canadian Medical Association Journal, Mar. 1952, pp. 278-279, vol. 66.
I. O. B. Spencer, "Ferrous Sulphate Poisoning in Children," The British Medical Journal, Nov. 1951, pp. 1112-1117.
Isabel Diaz del Consuelo, et al., "Transport of Fentanyl Through Big Buccal and Esophageal Epithelia in Vitro. Influence of Concentration and Vehicle pH," Pharmaceutical Research, Sep. 2005, pp. 1525-1529, vol. 22, No. 9.
Jay Umbreit, "Iron Deficiency: A Concise Review," American Journal of Hematology, 2005, pp. 225-231, vol. 78.
John M.C. Gutteridge, "Lipid Peroxidation and Antioxidant as Biomarkers of Tissue Damage," Clinical Chemistry, Sep. 1995, pp. 1819-1828, vol. 41, No. 12.
P. Geisser, et al., "Iron Pharmacokinetics After Administration of Ferric-Hydroxide-Polymaltose Complex in Rats," Arzneimittel Forschung—Drug Research, 1984, pp. Nr 11; 1560-1569, vol. 34, No. 2.
P. Geisser, et al., "Pharmacokinetics of Iron Salts and Ferric Hydroxide-Carbohydrate Complexes," Arznelmittel Forshung—Drug Research, 1987, pp. Nr 1a: 100-104, vol. 37, No. 1.
P. Jacobs, "Equivalent Bioavailability of Iron From Ferrous Salts and a Ferric Polymaltose Complex: Clinical and Experimental Studies," Arzneimittel Forschung—Drug Research, 1987, pp. Nr 1a: 113-116, vol. 37 No. 1.
Rashid A. Al-Rashid, "Syndromes of Iron Overload," Clinical Toxicology, Dec. 1971, pp. 571-578, vol. 4, No. 4.
Roger T. Dean, et al., "Biochemistry and Pathology of Radical-Mediated Protein Oxidation," Biochemical Journal (Great Britain), 1997, pp. 1-18.
Sherrod C. Swift, et al., "Ferrous Sulfate Poisoning," Journal of Pediatrics, 1952, pp. 6-10, vol. 40, No. 6.
Shigemasa Osaki, "Kinetic Studies of Ferrous Ion Oxidation with Crystalline Human Ferroxidase (Ceruloplasmin)," The Journal of Biological Chemistry, Nov. 1966, pp. 5053-5059, vol. 241, No. 21.
Shigemasa Osaki, et al., "The Possible Significance of the Ferrous Oxidase Activity of Ceruloplasmin in Normal Human Serum," The Journal of Biological Chemistry, Jun. 1966, pp. 2746-2751, vol. 241, No. 12.
Shinya Toyokuni, "Iron and Carcinogenesis: From Fenton Reaction to Target Genes," Redox Report, 2002, pp. 189-197, vol. 7, No. 4.
Thomas L. Duffy, et al., "Ferrous Sulfate Poisoning: Report of Three Cases," The Journal of Pediatrics, Jan. 1952, pp. 1-5, vol. 40, No. 1.
W. Forth, et al.; "Absorption of Di- and Trivalent Iron: Experimental Evidence," Arzneimittel Forschung—Drug Research, 1987, pp. Nr 1a: 96-100, vol. 37, No. 1.
W. Schneider, "The Fate of Iron Compounds in the Gastrointestinal Tract: Coordination-Chemical Facts," Arzneimittel Forschung—Drug Research, 1987, pp. Nr 1a: 92-95, vol. 37, No. 1.
A.E. Lichtin, "Iron Deficiency Anemia", The Merck Manual for Health Care Professionals, Nov. 2013, XP002721236, pp. 6/8-7/8, URL: http://www.merckmanuals.com/professional/hematology_and_oncology/anemias_caused_by_deficient_erythropoie.
Bernd Dresow et al: "Non-Transferrin-Bound Iron in Plasma Following Administration of Oral Iron Drugs", Biometals, Kluwer Academic Publishers, BO, vol. 21, No. 3, Sep. 13, 2007, pp. 273-276, XP019600299.
Celeketic et al: "P093 Treatment of Iron-Deficiency Enemia With Ferrous Gluconate", Blood Reviews, Churchill Livingstone, vol. 21, Aug. 1, 2007, pp. S117, XP022204764.
Database GNPD [Online] Mintel; Dec. 2012, "Fresh & Fruity Multivitamins", XP002721234, Database Accession No. 1944952.
Database GNPD [Online] Mintel; Jun. 2012, "Chewable Multivitamins for Kids", XP02721233, Database Accession No. 1827458.
Database GNPD [Online] Mintel; May 2013, "Multivitamin Fruit & Vegies", XP002721235, Database Accession No. 2078218.
International Report on Patentability dated Oct. 16, 2015 re: Application No. PCT/IB2014/001303; pp. 1-25.
International Search Report dated Dec. 12, 2014 re: Application No. PCT/IB2014/001303; pp. 1-5; citing: U.S. Pat. No. 4,058,621 A, L C Brumpt et al., Celeketic et al., Database Jun. 2012, Database Dec. 2012, Database May 2013, Lichtin and Dresow Bernd et al.
Written Opinion dated Dec. 12, 2014 re: Application No. PCT/IB2014/001303; pp. 1-6; citing: U.S. Pat. No. 4,058,621 A, L C Brumpt et al., Celeketic et al., Database Jun. 2012, Database Dec. 2012, Database May 2013, A.E. Lichtin and B. Dresow et al.
CN Office Action dated Nov. 1, 2017 re: Application No. 201480039686.3; pp. 1-16.
E. Werner, et al., "Judgement of Measured Values of Intestinal Iron Absorption," Arzneimittel Forschung—Drug Research, 1987, pp. Nr 1a: 116-121, vol. 37, No. 1.
L C Brumpt et al: "Comparison Between the Buccal and Rectal Routes of Administration of Ferrous Salts in the Treatment of Ancylostomal Anemia", Bulletin De La Societe De Pathologie Exotique Et De Ses Filliales, vol. 50, No. 1; Jan. 1957, pp. 75-78 (Concise Statement of Relevance is Enclosed).
Shojaei "Buccal Mucosa as a Route for Systemic Drug Delivery: A Review"; J. Pahrm. Pharmaceut. Sci.; 1998; 1(1); pp. 15-30 (www.ualberta.ca/-csps).

(56) References Cited

OTHER PUBLICATIONS

Zhen "Iron deficiency anemia and iron supplementation research progress", Foreign Medical Health Volume; 2006; vol. 33; No. 2; pp. 90-93 (English Translation).
Zhen "Iron deficiency anemia and iron supplementation research progress", Foreign Medical Health Volume; 2006; vol. 33; No. 2; pp. 90-93 (Non-English Translation).
Medicine Guide. Diagnostic and Therapy (Ed. R. Burkou M., The World 1997) (Concise English Summary Enclosed), (for p. 779, 2nd column, 3rd paragraph).
Mikhailov I.B. The doctor's reference book on clinical pharmacology (Concise English Summary Enclosed), *English summary found in English translation of Russian Office Action for Application No. 2016103912/15 (0006183), dated Aug. 3, 2018.
Russian Office Action; for Application No. 20161039122/15 (006183); dated Aug. 3, 2018; 7 pages (English Translation).
Russian Office Action; for Application No. 20161039122/15 (006183); dated Aug. 3, 2018; 7 pages (Non-English Translation).

* cited by examiner

MODUS OF ADMINISTRATION OF IRON, AND NEW FORMULATIONS ADAPTED FOR THE SAID GOAL

TECHNICAL FIELD

The present disclosure relates to a new modus and a new regimen of administration of divalent iron for hyposideremia therapy and to new formulations containing divalent iron compounds adapted to release the iron for intrabuccal absorption, preferably for sublingual absorption.

BACKGROUND

Iron metabolism has the particularity that it is controlled by absorption rather than by excretion: iron is eliminated mainly by means of the loss of cells of the mucosae and of the skin (approximately 1 mg per day). The total pool of iron in our body is approximately 4,000 mg, of which a little over 2,000 is in erythrocytes and in their precursors and 1,600-1,800 mg are in the form of deposit, while the amount of iron that can be found in serum is approximately 4 mg.

Lack of iron or hyposideremia, due often that not only to its malabsorption at the intestinal level, is one of the greatest causes of the forms of anemia that develop in children or adults. It is calculated that approximately 750 million people worldwide (Umbreit J., Am. J. Hematol. 2005; 78:225-231; Killip S., Bennet J. M., Chambers M. D., Am. Fam. Physician 2007; 75:671-678) are affected by this nutritional deficiency, particularly children, in which the iron deficiency can cause severe cognitive deficits, or in fertile or pregnant women, in which iron deficiency can cause premature birth and prenatal mortality. This deficiency is usually treated by administering divalent or trivalent iron. Divalent iron, in the form of salts or complexes, is administered generally orally (i.e., for absorption at the gastrointestinal level), while trivalent iron is administered only in the form of a complex both orally (i.e., for adsorption at the gastrointestinal level) and parenterally.

Therapy with Divalent Iron

Oral anti-hyposideremia therapy (i.e., for absorption at the gastrointestinal level) with salts or complexes of divalent iron (i.e., Fe(II), $Fe^{2+}$ or $Fe^{++}$), despite being normally effective, is characterized by some side effects that can limit its use severely. The oral administration of ferrous sulfate, ferrous ascorbate or other salts/complexes such as ferrous gluconate or citrate has as a first negative effect intolerance at the gastric level, which causes nausea, vomiting, epigastric pain such as to often encounter refusal of the therapy by the patient. Moreover, susceptibility to oxidation in the bowel portion of the duodenum-jejunum of divalent iron (in a neutral-basic environment, the most stable oxidation state of iron is the trivalent one) causes a drastic decrease in absorption, which is compensated by an increase in doses, which in turn increase the negative effects at the gastric level and not only. This leads in fact to another drawback, which is even more severe, i.e., toxicity at the systemic level. The maximum dose of divalent iron that can be administered orally in the therapy of sideropenic anemia, particularly of chronic sideropenic anemia, especially if applied for an extended time interval, for example two weeks to six months, oscillates between 150 and 450 mg per day for a human patient, depending on the severity of the disease and on the type of preparation used. The absorbed iron is usually carried and deposited in iron-deficient cells by protein (transferrin is one of the main iron carriers); however, if the quantity of iron absorbed is such as to saturate transferrin (or if absorption is faster than the complexing rate of transferrin) and is such as to circulate in ionized form in the blood as trivalent iron, toxicity conditions can occur. This non transferrin bound excess (so-called free iron or "NTBI"—non transferrin bound iron) manifests its toxicity by causing the formation of compounds based on reactive oxygen, such as the superoxide anion (O2-), hydrogen peroxide (H2O2) or the hydroxyl radical (OH.), all of which are capable of damaging cells by oxidizing protein, lipids and DNA itself (Gutteridge J. M. Lipid peroxidation and antioxidants as biomarkers of tissue damage. Clin. Chem. 1995; 41:1819-1828; Stadtman E. R., Berlett B. S. Reactive oxygen-mediated protein oxidation in aging and disease. Chem. Res. Toxicol. 1997; 10:485-494; Dean R. T., Fu S., Stocker R. et al. Biochemistry and pathology of radical-mediated protein oxidation. Biochem. J. 1997; 324 (Pt 1): 1-18; Henle E. S., Linn S. Formation, prevention, and repair of DNA damage by iron/hydrogen peroxide. J. Biol. Chem. 1997; 272:19095-19098; Toyokuni S. Iron and carcinogenesis: from Fenton reaction to target genes. Redox Rep. 2002; 7: 189-197).

This toxicity of divalent iron can occur both in the adult and in the child, in which the outcome can even be fatal.

In these cases, therefore, the patient rapidly reaches a level of serum iron that is higher than desired, entering a state of hypersideremia; in these conditions, the patient is exposed to an oxidative stress which is due to high blood levels of iron [Al-Rashid, Rashid A, (1971) Clinical Toxicology, 4:4, 571-578; Witzleben C. L. and Buck B. E. (1971) Clinical Toxicology 4:4, 579-583; K. R. Reissmann and T. J. Coleman, (1955) 10: 46-51]. Through the years there has been an important number of deaths due to hypersideremia in children after oral administration of iron sulfate or other divalent iron salts. Regrettably, these deaths have demonstrated that the definition of the therapeutic window for oral administration of divalent iron entails considerable difficulties (Reissmann K. R, Coleman T. J, Budai B. S. and L. R. Moriarty, (1955) 10:35-45; Editorial: Acute iron poisoning in children. Canad. M. A. J. 66: 278, 1952.; Swift, S. C., Cefalu, V., and Rubell, E. B.: Ferrous sulfate poisoning J. Pediat. 40: 6, 1952; Duffy, T. L., and Diehl, A. M.: Ferrous sulfate poisoning. J. Pediat. 40: 1, 1952). Part of the toxicity of the Fe++ administered orally is attributed in many publications to its direct action on intestinal mucosa, which is necrotized, with severe hemorrhagic events (Spencer, I. O. B.: Ferrous sulfate poisoning in children. Brit. M. J. 2: 1112, 1951).

Therapy with Trivalent Iron

Trivalent iron (i.e., Fe(III), $Fe3^{+}$ or $Fe^{+++}$), differently from reduced iron, can be absorbed only at extremely acid pH levels, distinctly lower than 2.0, since only in these conditions is it stable as a cation and does not precipitate. For this reason, oral administration (i.e., for absorption at the gastrointestinal level) of trivalent iron salts finds no application, since the pH close to neutrality of the duodenum-jejunum intestinal tract, which is the portion assigned to iron absorption, causes its precipitation, making its absorption impossible. Oral administration of trivalent Fe has instead been made possible by using complexing agents such as citrate anions, EDTA and others—or mono and disaccharides, which are able, again by complexing, to render soluble even trivalent Fe in the form of hydroxide oxide (FeOOH). Therefore, in these conditions the trivalent iron contained in the complexes cited above, by not precipitating at the level of the duodenum-jejunum tract, remains bioavailable for gastrointestinal absorption and is therefore usable for oral administration.

Moreover, these Fe+++ complexes, administered orally, do not produce the side effects of Fe++ salts.

However, the drawback observed in the development of these complexes is associated with the difficulty in studying their pharmacokinetics in healthy volunteers. It would appear in fact that the extent of the absorption of these compounds depends on the need of said individual to increase iron levels (W. Forth and S. G. Schäfer, Arzneim.-Forsch./Drug. Res. 37(I), Nr 1a: 96-99 (1987); P. Geisser and A. Müller, Arzneim.-Forsch./Drug. Res. 37(I), Nr 1a: 100-104 (1987); P. Geisser and A. Müller, Arzneim.-Forsch./Drug. Res. 34(II), Nr 11: 1560-1569 (1984); W. Schneider, Arzneim.-Forsch./Drug. Res. 37(I), Nr 1a: 92-95 (1987); P. Jacobs, Arzneim.-Forsch./Drug. Res. 37(I), Nr 1a: 113-116 (1987); E. Werner and J. P. Kaltwasser, Arzneim.-Forsch./Drug. Res. 37(I), Nr 1a: 116-121 (1987)).

The results obtained with studies conducted on anemic patients would appear to show that serum iron levels observed following oral administration of ferrous sulfate or iron oxide hydroxide that has been complexed (for example with a maltodextrin) are entirely comparable. The subject is in any case still at the center of a debate, since the various pharmacokinetics that have been performed with unmarked trivalent iron complexes taken orally have yielded ambiguous results. This may be due also to the fact that complexes of ferro-maltodextrin (so-called ferric polymaltose) obtained with different synthetic methods have shown different stability and chemical-physical characteristics; the data obtained in pharmacokinetics studies therefore are not often comparable. Of the Fe+++ complexes studied for their use in oral therapy, only ferric polymaltose is currently commercially available.

Having therefore evaluated the negative aspects associated with the oral administration of compounds based on divalent and trivalent Fe, it has been thought to use another modus of administration capable of bypassing the digestive system without however resorting to the parenteral pathway. This is done to allow easy anti-anemic therapy even for patients affected for example by inflammatory bowel diseases (for example IBD or celiac disease) without however resorting to the intravenous pathway, which is more expensive and is characterized by important side effects.

The literature reports various attempts to allow administration of various substances, including iron, by means of a pathway that is different from the gastrointestinal or parenteral one. However, as regards therapy of hyposideremia, the drugs currently commercially available are preset for the oral pathway or for the parenteral pathway.

In view of what has been described above, it appears therefore evident that currently there are no formulations of iron for treatment, preferably prolonged treatment, of hyposideremia or of its most severe states, such as malabsorption of iron due to celiac disease or chronic inflammatory bowel diseases, or sideropenic anemia due to blood losses, which are easy to manage and are not associated with important unwanted effects.

The present disclosure therefore provides compounds of iron and new formulations of iron that are not parenteral and allow an alternative to classic oral, i.e., gastrointestinal, administration, in the therapy of hyposideremia or of its more severe states, avoiding advantageously the drawbacks associated with gastrointestinal administration of salts of divalent Fe or of complexes of trivalent iron. By means of the development of these formulations, facilitated treatment also becomes possible of anemic states in patients that do not tolerate oral therapy (i.e., by absorption at the gastrointestinal level), such as for example patients affected by chronic inflammatory bowel diseases (IBD) or by celiac disease, thus avoiding parenteral therapy.

The present disclosure further provides new formulations of iron that are not parenteral and exhibit a reduced toxicity with respect to classic formulations of divalent iron that are administered orally.

The present disclosure also provides new formulations of divalent iron that are effective for the therapy of anemic states due to malabsorption of iron caused by celiac disease or chronic inflammatory bowel diseases or due to chronic sideropenic anemia caused by blood losses at lower dosage regimens than oral preparations (i.e., with gastrointestinal absorption) that are currently commercially available, thus lowering favorably the risk/benefit ratio of the therapy.

SUMMARY

A series of studies conducted now by the inventors of the present application has shown that the modus of administration suitable for the mentioned purposes is the one associated with the intrabuccal, more preferably sublingual, absorption of divalent iron salts. Intrabuccal absorption has not yet been considered and explored for the purposes described here, as is apparent from the following overview:

U.S. Pat. No. 4,058,621 relates generically to complexes of galacturonate or glucuronate that comprise iron for administration to mammals However, U.S. Pat. No. 4,058,621 does not describe the administration to human beings of divalent iron by means of the above cited complexes. Most of all, U.S. Pat. No. 4,058,621 does not teach intrabuccal or sublingual administration and much less teaches this type of administration to reduce the onset of free iron with respect to gastrointestinal administration.

In fact, U.S. Pat. No. 4,058,621 does not raise the problem of the toxicity of free iron and rather teaches to dose the active ingredient by providing a certain safety margin with respect to the oral LD50 (of iron(II) sulfate) according to the literature. Taking oral LD50 as reference, it appears that U.S. Pat. No. 4,058,621 considers formulations in chewing gum form as forms of oral administration (see also the comment below regarding chewable tablets). U.S. Pat. No. 4,058,621 in fact contains no in vitro or in vivo exploration regarding intrabuccal administration, its effectiveness if any, and/or a possible (negative or positive) influence of the relationship between pharmacological activity and side effect that might arise from it. The doses reported by U.S. Pat. No. 4,058,621, therefore, are not described for intrabuccal administration.

Brumpt et al. "Comparison between the buccal and rectal routes of administration of ferrous salts . . . ", Bulletin de la Société de Pathologie Exotique et ses Filiales, Vol. 50, no. 1, January 1957, p. 75-78, describes a comparison between rectal administration (suppository) and oral (gastrointestinal) administration of ferrous sulfate/gluconate. In particular, the authors demonstrate that oral administration is more effective than rectal administration, with faster and higher increases in hemoglobin levels. The authors use the term "buccal" to describe administration via the mouth (=oral) in order to obtain gastrointestinal absorption. This is highlighted in the conclusions of the publication, in which the authors point out that the superior result of buccal administration with respect to the rectal pathway was not considered truly surprising in view of the fact that it was already known at the time that iron absorption occurs at the level of the duodenum. Therefore, it is clear that the authors, by "buccal" administration, do not intend intrabuccal administration, i.e., through the buccal mucosae.

The Tot'hema preparation mentioned in Celeketic et al. "Treatment of iron-deficiency anemia with ferrous gluconate", Blood Reviews, Churchill Livingstone, Amsterdam, NL, vol. 21, Aug. 1, 2007 page S117 is a drinkable solution that is marketed in vials comprising 50 mg of Fe. The content of the vial is administered to the patient by dilution in a beverage, see for example http://www.innotech.lv/index.php?cat_id=2&prod_id=23&t=eng/prod. Therefore, the absorption of Tot'hema occurs at the gastrointestinal level.

In the background art, products are known which comprise iron salts and are made available in the form of chewable tablets. Examples of this class of products are "Chewable Multivitamins for kids" (Bayer—"Penta-Vite", as advertised on June 2012 on the Internet and registered in the Mintel GNPD Database with access no. 1827458), "Fresh & Fruity Multivitamins" (Pfizer—"Centrum", as advertised in December 2012 on the Internet and registered in the Mintel GNPD Database with access no. 1944952) or "Multivitamin Fruit & Vegies" (Sanofi-Aventis—"Cenovis Kids Vita Tingles", as advertised in May 2013 on the Internet and registered in the Mintel GNPD Database with access no. 2078218. As regards these formulations, it should be considered that a chewable tablet is a pharmaceutical form for oral, i.e., gastrointestinal, administration. The chewable tablet, in addition to the fact that it can be swallowed directly like a classic tablet, can be ingested easily even without water by the patient, in particular by children or geriatric patients, without having to swallow the entire tablet. Therefore, the chewable tablet, in the absence of other specific indications, does not necessarily produce an intrabuccal absorption. Most of all, in the absence of specific indications, the chewable tablet cannot produce a definite or repeatable transmucosal absorption in the buccal apparatus.

It should be stressed that the same applies for a chewing gum as considered by U.S. Pat. No. 4,058,621 discussed above. This occurs because chewing stimulates salivation, which increases swallowing and therefore—again in the absence of specific indications—determines the gastrointestinal absorption of the active ingredient released by the formulation.

US 2003/082107 relates to intrabuccal formulations proposed for a large quantity of active ingredients of entirely different chemical and pharmacological classes. While it mentions, among these, also ferrous sulfate, the latter is not indicated by US 2003/082107 as anti-anemic, but rather as an antidote, i.e., in order to contrast poisonings. US 2003/082107 also lacks any data (in vitro or in vivo) regarding the effectiveness of intrabuccal administration for any concrete active ingredient. Much less does US 2003/082107 explore how intrabuccal administration might influence the relation between sought pharmacological effect and side effect for a given active ingredient.

The overview as mentioned above, therefore, shows that intrabuccal administration of divalent iron for anti-anemic purposes was neither described nor considered in the background art. Much less were the adapted doses known, neither for producing an appreciable pharmacological effect nor much less for reducing side effects with respect to gastrointestinal administration.

Instead, in vitro and in vivo studies performed for the first time by the inventors of the present application have shown now that the absorption of divalent iron compounds by means of the mucosae of the mouth (i.e., so-called intrabuccal administration), particularly sublingual mucosae, is not only effective at a physiological level but also that this intrabuccal or sublingual administration is even more effective than classic gastrointestinal absorption, which, for an equal increase in transferrin saturation, is instead more susceptible to the onset of toxicity correlated with free iron. Therefore, in view of this discovery and with the goal of achieving the above cited aim, the present disclosure, in a nonexclusive embodiment thereof provides divalent iron compounds for use in hyposideremia therapy by administration through intrabuccal absorption in a patient, in which administration occurs with the indication to the patient to avoid swallowing the formulation containing the divalent iron compound and/or saliva for a period of time of at least 30 seconds after placing the formulation containing the divalent iron compound in the intrabuccal cavity, said use providing for the administration of divalent iron at doses comprised in an interval between 1-90 mg of divalent Fe per day for a human patient in order to reduce, for an equal increase in transferrin saturation, the onset of free non transferrin bound iron with respect to gastrointestinal administration.

In a further nonexclusive embodiment, the present disclosure provides formulations of divalent iron with intrabuccal absorption, in which the divalent iron compound is constituted preferably by a salt or a complex of divalent iron which is soluble at pharmaceutical acceptable pH values for administration through intrabuccal absorption, said formulation being preset in individual doses comprised in an interval ranging from 0.5 to 30 mg of divalent iron for use in hyposideremia therapy in a patient, in which therapy administration occurs with the indication to the patient to avoid swallowing the formulation containing the divalent iron compound and/or saliva for a period of time of at least 30 seconds after placing the formulation containing the divalent iron compound in the intrabuccal cavity, in order to reduce, for an equal increase in transferrin saturation, the onset of free non transferring bound iron with respect to gastrointestinal administration.

This is done because, as will become apparent hereinafter, the inventors of the present application have found that administration through intrabuccal, preferably sublingual, absorption of a divalent iron compound according to the present disclosure allows to obtain in the patient an increase in transferrin saturation that is comparable to the one produced by gastrointestinal administration (i) at a dose that is reduced by at least 50%, and (ii) with an onset of non transferrin bound iron that is reduced at least by 75% with respect to gastrointestinal administration.

Within the scope of the embodiment described above, use in the therapy of the most severe states of hyposideremia, such as of iron malabsorption due to celiac disease or chronic inflammatory bowel diseases or chronic sideropenic anemia due to blood losses, occurs by administration through intrabuccal absorption, preferably through sublingual absorption in a patient, said use providing for the administration of divalent iron at doses comprised in an interval from 10 to 90 mg of divalent Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient. The doses cited above are lower than the doses (with gastrointestinal administration) normally prescribed for the above cited severe hyposideremia states, and therefore the provision of these reduced doses is—on its own—provided by the present disclosure. Moreover, according to a further aspect of the present disclosure, these doses are used preferably to reduce, for an equal increase in transferrin saturation, the onset of free non transferrin bound iron with respect to gastrointestinal administration.

In a further embodiment, the present disclosure provides divalent iron compounds for use in the therapy of relapsing anemic states, which have been treated previously with gastrointestinal therapy with compounds of divalent or trivalent iron or have been treated previously with parenteral therapy with trivalent iron compounds, said use providing for administration through intrabuccal absorption, preferably sublingual absorption, of the divalent iron compound to the patient.

In a further embodiment, the present disclosure provides an anti-hyposideremic medical composition with release for intrabuccal absorption, preferably for sublingual absorption, comprising divalent iron for use in therapy with doses comprised in an interval between 1-90 mg of divalent Fe per day for a human patient, preferably 1 to 60 mg of divalent Fe per day for a human patient, more preferably from 4 to 40 mg of divalent Fe per day for a human patient, even more preferably from 5 to 30 mg of divalent Fe per day for a human patient.

All the dosage intervals described in the present application apply to a human adult patient; however, the person skilled in the art, on the basis of the indications given herein, may adapt the doses used in practice to the requirements of children and/or to the severity of the case, selecting, according to the circumstances, values that are close to the lower or upper limit of the indicated intervals.

Preferably, said anti-hyposideremic medicinal composition based on divalent iron for intrabuccal absorption, preferably for sublingual absorption, is preset in individual doses comprised in an interval from 0.5 to 30 mg of divalent Fe, preferably from 3 to 20 mg of bivalent Fe, more preferably 3 to 10 mg of divalent Fe. Further embodiments and preferred variations thereof are described hereinafter.

BRIEF DESCRIPTION OF THE DRAWINGS

The curve recorded with 50 mg/ml of divalent Fe ascorbate and in the presence of ascorbic acid reaches a value above 150 micrograms/square centimeter after 3 hours and a value of approximately 200 micrograms/square centimeter after 4 hours (see pale blue squares).

The curve recorded with 350 mg/ml of divalent Fe ascorbate and in the presence of ascorbic acid reaches a value just below 150 micrograms/square centimeter after 3 hours and a value of approximately 200 micrograms/square centimeter after 4 hours (see purple squares).

The curve recorded with 400 mg/ml of divalent Fe ascorbate and in the absence of ascorbic acid reaches a value just above 100 micrograms/square centimeter after 3 hours and a value of approximately 150 micrograms/square centimeter after 6 hours (see purple diamonds).

The curve recorded with 600 mg/ml of divalent Fe ascorbate and in the absence of ascorbic acid reaches a value just above 100 micrograms/square centimeter after 3 hours and a value of approximately 125 micrograms/square centimeter after 6 hours (see red squares).

The curve recorded with 1000 mg/ml of divalent Fe ascorbate and in the absence of ascorbic acid reaches a value of approximately 50 micrograms/square centimeter after 3 hours and a value of approximately 100 micrograms/square centimeter after 5 hours (see green triangles).

FIG. 3 is a permeation chart of the solution of ferric citrate (Fe+++) obtained in the Franz cell. The vertical axis plots the permeated trivalent Fe (in micrograms per square centimeter of membrane), while the horizontal axis plots time (in hours). After 4 hours, a little under 11 micrograms of trivalent iron per square centimeter have permeated.

DETAILED DESCRIPTION OF THE DRAWINGS

As shown in the summary, the inventors of the present application have found surprisingly that the mentioned aims of the disclosure are to provide new formulations for intrabuccal absorption, preferably sublingual absorption, of divalent iron compounds.

Intrabuccal or preferably sublingual administration according to the present disclosure occurs by administration of an adapted formulation applied in the oral cavity, preferably under the tongue of the patient, with an indication to the patient to avoid swallowing the formulation containing the divalent iron compound and/or saliva for a period of time of at least 30 seconds, preferably at least one minute, more preferably at least two minutes, even more preferably at least four minutes after placing the formulation containing the divalent iron compound in the intrabuccal cavity, preferably under the tongue.

Compounds of divalent iron that can be used for the purposes of the present disclosure are understood to be all compounds, including salts and complexes, with pharmaceutically acceptable anions, of divalent iron that are soluble at the physiological pH of the site of administration, i.e., at the intrabuccal pH of a human patient, or at values of pH that can be tolerated in the intrabuccal administration site, such as for example pH 2.0-8.0, preferably pH 2.0-6.5, more preferably pH 2.5-4.5. Preferred but not exclusive examples of divalent iron compounds are therefore salts and complexes of divalent iron already currently used in classic oral therapy, including, for example, the group consisting of ferrous sulfate, ferrous citrate, ferrous ascorbate, ferrous fumarate, ferrous glycinate, ferrous gluconate and others. Among the divalent compounds considered by the present disclosure, preference is given to Fe++ ascorbate.

The expression "intrabuccal formulations" is understood to reference all formulations preset and indicated to release the active ingredient so as to allow its absorption through the intrabuccal mucosa, preferably through the sublingual mucosa, such as, merely by way of example: intrabuccal tablets, sublingual tablets, so-called oral drug strips (i.e., intrabuccal or sublingual films), so-called wafers (i.e., intrabuccal or sublingual flat elements), granulated or powdered material, sprays, foams, gels or intrabuccal paste. Preferably, the tablets, strips (films) and wafers (flat elements) are prepared in film form.

"Film form" means that the tablets, films or flat elements according to the disclosure, differently for example from traditional tablets, are characterized by a reduced thickness and are preferably flexible. Moreover, they are preferably preset to adapt, after absorbing humidity, to the oral mucosa, such as for example the palate or the sublingual or gingival region. The total thickness of the film forms (prior to application) amounts preferably to 0.05 to 3 mm, more preferably 0.1 to 1 mm, and even more preferably to 0.1 to 0.5 mm. The film forms can have a round, oval, triangular, quadrangular or multi-angular area shape. Their area amounts preferably to 0.5 to 20 cm$^2$, preferably 1 to 10 cm$^2$.

Moreover, the film forms (but not only those) may have mucoadhesiveness characteristics indeed to allow correct absorption in the sublingual or palate region and can release the divalent iron completely with times that can vary from a few seconds to a few minutes. Preferably, the solid formulations according to the present disclosure are characterized in that they break down rapidly in aqueous environments, preferably in saliva, preferably within 10 seconds to 5 minutes, more preferably within 30 seconds to 3 minutes, even more preferably within 1 and 2 minutes, releasing the entire divalent iron compound. It is advantageous that the film forms to be applied/stuck to the palate or to the sublingual region, which can comprise both rapid-breakdown tablets (so-called "fast-melt" tablets) and films or strips with immediate or delayed release, can be administered in a simple, inconspicuous and safe manner, without further addition of liquids (as occurs instead for tablets to be swallowed), thus achieving excellent patient compliance.

In view of the characteristics of absorption through buccal mucosae of the divalent iron compounds discovered by the inventors of the present application, the above cited divalent iron formulations are in fact believed to be suitable to ensure an intrabuccal absorption, preferably sublingual absorption, of divalent iron compounds that is repeatable, regular in its quantity and required time, without resorting to high doses.

The high absorption of the iron II compounds at the intrabuccal level, more preferably sublingual level, thus makes it possible to provide new anti-sideremic medicinal compositions with release for intrabuccal absorption, preferably sublingual absorption, comprising divalent iron, which lend themselves to therapy of pathological deficiencies of iron and/or hemoglobin with varying degrees of severity.

In some cases, hyposideremia is determined by an iron deficiency, such as anemia associated with chronic or acute blood loss, pregnancy, childbirth, infant growth, psychomotor development, severe uterine hemorrhages, menstruations, chronic relapsing hemoptysis, parasite infections, chronic kidney diseases and dialysis, surgical procedures or acute traumas, chronic ingestion of alcohol or steroids, chronic ingestion of NSA (nonsteroidal anti-inflammatory agents) or chronic ingestion of erythropoiesis stimulating agents. In other cases, hyposideremia can be an anemia associated with other diseases, such as rheumatoid arthritis, cancer, Hodgkin's leukemia, non-Hodgkin's leukemia, anti-cancer chemotherapy, bowel inflammation (IBD), ulcerative colitis, thyroiditis, hepatitis, systemic lupus erythematosus, rheumatic polymyalgia, scleroderma, connective tissue diseases, Sojgren's syndrome, congestive heart failure/cardiomyopathy, or geriatric idiopathic anemia. In other cases also, hyposideremia can be due to disorders in iron absorption, such as for example anemias associated with Crohn's disease, gastric surgery, ingestions of drugs that inhibit iron absorption or chronic ingestion of calcium.

Anti-hyposideremic medicinal compositions according to the present disclosure are preferably indicated for administration through intrabuccal, preferably sublingual, absorption of divalent iron with doses comprised in an interval from 1 to 90 mg of divalent Fe per day for a human patient, preferably 1 to 60 mg of divalent Fe per day for a human patient, more preferably 4 to 40 mg of divalent Fe per day for a human patient, even more preferably 5 to 30 mg of divalent Fe per day for a human patient, with the aim of restoring biological levels in the patient affected by hyposideremia, in order to reduce, for an equal increase in transferrin saturation, the onset of free non-transferrin bound iron with respect to gastrointestinal administration.

According to the present disclosure, the doses cited above can be modified preferably in severe cases of hyposideremia, such as (i) malabsorption of iron due to celiac disease or chronic inflammatory bowel diseases or (ii) of chronic sideropenic anemia due to blood losses. Chronic sideropenic anemia due to blood losses is linked to the following phenomena:

excessive blood loss during menstrual cycles. Moreover, in women of fertile age, a further need is constituted by pregnancy and puerperium.

blood losses at the level of the digestive tract. Normally, less than 1 ml of blood per day is lost through this pathway, but some pathological conditions entail daily losses of 10-20 ml or more. In Western countries, the most common causes of these losses are, in order of importance, hemorrhoids, peptic ulcer, chronic use of acetylsalicylic acid and other types of FANS, hiatal hernia, colonic diverticulosis and bowel tumors. In developing countries, the main cause is constituted by bowel parasitoses.

In severe cases of hyposideremia (i) and (ii), the doses are preferably comprised in an interval from 10 to 90 mg of divalent Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient. Particular preference is given to an interval ranging from 45 to 65 mg of divalent Fe per day for a human patient. It should be stressed that the provision of doses as above for severe disorders is new and arises from the higher efficiency of the compositions described here in saturating transferrin.

In view of the capabilities of the new compositions described here, the anti-hyposideremic medicinal compositions according to the present disclosure are also indicated in the therapy of relapsing anemic states treated previously with gastrointestinal therapy with compounds of divalent or trivalent iron, or treated previously with parenteral therapy with trivalent iron compounds. In these cases, the doses can be reduced with respect to the previous therapy. Therapy of relapsing anemic states can occur preferably at doses comprised in an interval from 1 to 90 mg of divalent Fe per day for a human patient, preferably 1 to 60 mg of divalent Fe per day for a human patient, more preferably 4 to 40 mg of divalent Fe per day for a human patient, even more preferably 5 to 30 mg of divalent Fe per day for a human patient, with the purpose of restoring biological levels in the patient affected by relapsing anemic states.

In severe cases of relapsing anemia caused by (i) iron malabsorption due to celiac disease or chronic inflammatory bowel diseases or (ii) chronic sideropenic anemia due to blood losses, the doses applied are generally higher, preferably comprised in an interval from 10 to 90 mg of divalent Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient. Again within the scope of sublingual therapy, in cases (i) and (ii), particular preference is given to a dose comprised in an interval from 45 to 65 mg of divalent Fe per day for a human patient.

The doses cited above arise from a study conducted by the inventors of the present application and aimed at evaluating the intrabuccal/sublingual absorption of divalent iron. Surprisingly, it has been found that the tested divalent iron compounds, placed in contact with pig esophageal epithelium (a scientifically recognized model for in vitro study of absorption through intrabuccal and/or sublingual mucous tissue), were able to penetrate through the epithelium, thus demonstrating that they could be absorbed. On the contrary, the complex of iron oxide hydroxide with maltodextrins already used in traditional oral therapy, placed in the same operating conditions, is not absorbed. For Fe+++ citrate, instead, absorption remains lower and is appreciable only at very low pH values. According to a preferred embodiment, the anti-hyposideremic formulations with intrabuccal absorption, preferably with sublingual absorption, discovered by the inventors can be prepared by including buffering excipients and/or reducing excipients, with the aim of ensuring the solubility of the administered divalent compounds, preferably in the sublingual region. In this manner it is not necessary to administer high doses of drug to appreciate an effective absorption thereof, differently from what can occur in classic oral therapy.

In particular, by varying some operating parameters, such as the concentration of the iron salt in the solution being considered, the pH of the solution itself, etc., it has been noted that in in vitro studies performed by the inventors, in the experimental model used, concentration would appear to influence sublingual absorption of divalent iron in some cases in an inversely proportional manner, while the pH of the solution being considered, preferably maintained by means of the presence of buffering agents and/or the presence of reducing agents (antioxidants), influences most of all the stability of the ferrous ion.

For trivalent iron salts there is instead an intrabuccal absorption, preferably sublingual absorption, in the in vitro model only if the pH of the solution that contains them is distinctly lower than 2.0, preferably lower than 1.5, presumably because the Fe+++ is in appreciable quantities in a soluble cationic form only below this threshold of pH. Exclusively in these extreme pH conditions, absorption of trivalent salts is appreciable. It should also be considered that said extreme pH conditions would have to be maintained, in a hypothetical intrabuccal administration of ferric salts (Fe+++), for the entire period of time of absorption, which would make it necessary to include in the intrabuccal formulation a buffering system with a buffering capacity sufficient to ensure the pH distinctly lower than 2.0, preferably lower than 1.5, in the buccal cavity despite salivation (the pH of human saliva is between 6.5 and 6.9 and can rise up to 7.2 after stimulation of secretion).

Whereas instead for complexes of Fe+++ soluble at all pH values comprised between 1.5 and 10, such as for example ferric polymaltose, it has been found instead that the excessively high molecular weight inhibits passage through buccal mucosa, as represented in the experimental model used.

Vice versa, the Fe++ compounds used in the formulations according to the present disclosure, particularly the ferrous salts/complexes preferred by the disclosure, are compounds in which the iron is in its ionic form, which is soluble practically at all pH values comprised between 2.0 and 8.0, and therefore can be formulated and absorbed more easily for the intrabuccal pathway, preferably sublingual pathway.

The inventors believe that in this manner, intrabuccal administration allows to avoid the side effects due to contact of divalent iron with gastric mucosa; moreover, by using relatively low daily doses, which can be administered preferably by means of reduced single doses of divalent iron in the context of anti-hyposideremic therapy, one avoids high absorption peaks, with which toxicity due to saturation of circulating transferrin is often correlated. It should be noted that divalent iron, once absorbed through the sublingual pathway, rapidly makes contact with blood proteins, including ceruloplasmin or ferroxidase (Osaki, S., Kinetic Studies of Ferrous Ion Oxidation with Crystalline Human Ferroxidase (Ceruloplasmin). J. Biol. Chem., 241, 5053 (1966); Osaki, S., Johnson, D. A., and Ieden, E., J. Biol. Chem., 241, 2746 (1966)), being oxidized immediately to trivalent iron (Fe+++), which is captured by transferrin and carried to the sites of use or to deposits.

Clinical studies conducted by the inventors of the present application have in fact demonstrated that sublingual administration of divalent Fe according to the present disclosure allows to achieve an appropriate increase in the percentage of transferrin saturation (comparable to that obtained through the gastrointestinal pathway), using reduced doses (for example doses reduced by at least 50%, preferably at least 60%, with respect to the classic oral administration of the same compound of divalent iron), achieving, for example two hours after administration, substantially an equal increase in saturation accompanied at the same time by a reduction of the correlated risk (the free non transferrin bound iron is reduced by at least 75%, preferably at least 80%, more preferably at least 90%, with respect to classic oral administration of the same divalent iron compound), thus improving significantly the risk/benefit ratio linked to hyposideremia therapy.

Moreover, in the field of intrabuccal administration, preferably sublingual administration, it is possible to administer the divalent iron preferably at the optimum pH for absorption with the addition of adapted buffer systems. This can occur by including in the formulation pharmacologically acceptable buffer systems in a quantity suitable to obtain a pH between 2.0 and 6.5, preferably between 2.5 and 4.5, in the oral cavity of the patient during the initial step after the placement of the formulation in the oral cavity, preferably during 10 seconds to 5 minutes, more preferably 15 seconds to 3 minutes, even more preferably 20 seconds to 2 minutes.

To allow the characteristics described above to be present in the formulations according to the present disclosure, formulations with intrabuccal or preferably sublingual absorption are obtained which are preset in individual doses ranging from 0.5 to 30 mg of divalent Fe, preferably ranging from 3 to 20 mg of divalent Fe, more preferably ranging from 3 to 10 mg of divalent Fe for use in hyposideremia therapy in a patient.

In addition to the divalent iron compound, the formulations according to the present disclosure can also comprise additional active ingredients, such as for example folic acid.

The disclosure is described in greater detail hereinafter with a nonlimiting intent in the following examples.

EXAMPLE 1

Figure 1:
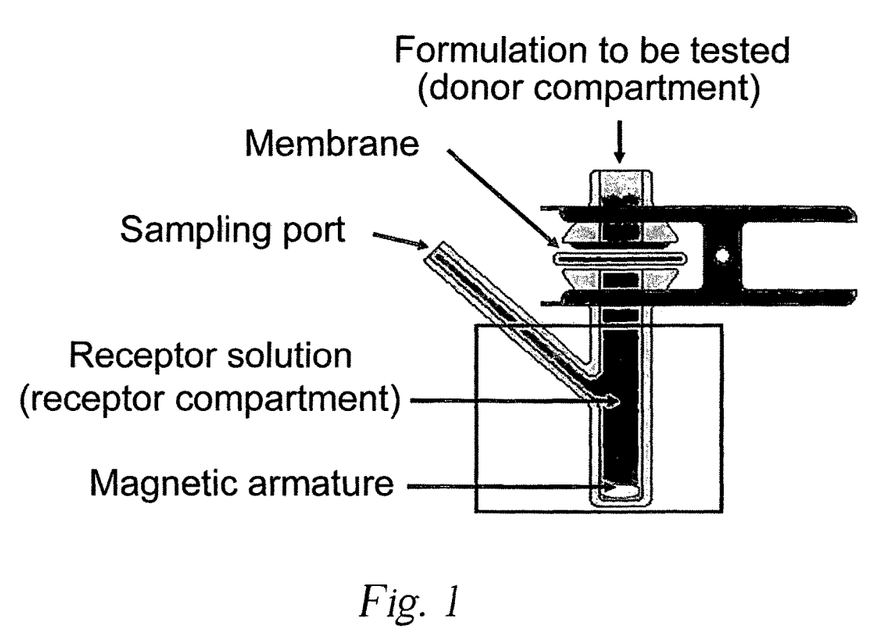
FIG. 1 is a schematic view of the Franz cell as used in the in vitro experiments described herein.

Sublingual absorption of Fe++ compounds was evaluated by means of in vitro permeation experiments using the Franz cell exemplified in FIG. 1. Pig esophageal epithelium was used as membrane. This experimental model is recognized as valid and reliable in the assessment of sublingual absorption of drugs [I. Diaz Del Consuelo, G. P. Pizzolato, F. Falsom, R. H. Guy, and Y. Jacques.: Evaluation of pig esophageal mucosa as a permeability barrier model for buccosal tissue. J. Pharm. Sci. 94: 2777-88 (2005); I. Diaz Del Consuelo, Y. Jacques, G. P. Pizzolato, R. H. Guy, and F. Falsom: Comparison of the lipid composition of porcine buccal and esophageal permeability barriers. Arch. Oral Biol. 50: 981-7 (2005); I. Diaz Del Consuelo, F. Folsom, R. H. Guy, and Y. Jacques: Transport of fentanyl through pig buccal and esophageal epithelia in vitro: influence of concentration and vehicle pH. Pharm Res. 22: 1525-9 (2005)]. Membrane preparation occurred by following the method described here. The esophagi were taken from the animals within one hour after sacrifice. The mucosa was separated from the muscle tissue with a lancet. To separate the epithelium, the mucosa was immersed in distilled water at 60° C. for 2 minutes and then the epithelium was removed from the underlying tissue with the aid of a spatula. The tissues thus prepared were stored at −20° C. until the time of use, when they were thawed to room temperature before being mounted on the vertical diffusion cells of the Franz type, a schematic view of which is shown in FIG. 1. The esophageal epithelium was placed on a regenerated cellulose filter (pore diameter 0.45 µm) with the luminal side facing up, and mounted between the donor and receptor compartments of the Franz cells. The filter only acts as a support and does not interfere with permeation of the active ingredient. The exposed surface was 0.6 cm$^2$. The receptor compartment was filled with approximately 4 ml of physiological solution (0.9% NaCl w/v) and kept under constant magnetic agitation for the entire duration of the experiment. The entire system was thermostat-controlled at 37° C. Sampling of the receptor compartment was performed by drawing 200 µl of receptor solution, which were replaced immediately with an equal volume of fresh physiological solution. The samples were taken at preset time intervals, specifically at 0, 1, 2, 3, 4, 5 and 6 hours.

EXAMPLE 2

Solutions of Fe++ ascorbate at different concentrations, with and without the addition of ascorbic acid, were prepared and measured in the Franz cell according to Example 1:

400 mg/ml Solution 4 g of powder were suspended in 10 ml of physiological solution and left under agitation for 15 minutes, then the solution was filtered with regenerated cellulose filters (pore diameter 0.45 µm). The concentration of Fe++ ascorbate was found to be 397.92±25.78 mg/ml. The pH was equal to 4.4.

600 mg/ml Solution 6 g of powder were suspended in 10 ml of physiological solution. The suspension was left under magnetic agitation for 25 minutes and then filtered with regenerated cellulose filters (pore diameter 0.45 µm). The concentration of Fe++ ascorbate was found to be equal to 638.84 mg/ml. The pH was equal to 4.4.

1000 mg/ml Solution 7 g of powder were suspended in 6 ml of physiological solution. The suspension was left under magnetic agitation for 1 hour; at the end it was filtered with regenerated cellulose filters (pore diameter 0.45 µm). The concentration of Fe++ ascorbate that corresponded to solubility was found to be 984.72±74.47 mg/ml. The pH was equal to 4.4.

50 mg/ml Solution with Addition of Ascorbic Acid, pH 2.6

250 mg of Fe++ ascorbate were dissolved in 5 ml of physiological solution. An excess of ascorbic acid (2 g) was added to the solution. The suspension was left under magnetic agitation for 30 minutes and after filtration through regenerated cellulose filters (pore diameter 0.45 µm) was used as it was. The pH of the solution was 2.6.

350 mg/ml Solution with Addition of Ascorbic Acid.

1.05 g of Fe++ ascorbate were dissolved in 3 ml of physiological solution. The solution received the addition of an excess of ascorbic acid (525 mg) and the pH of the solution was returned to the initial value of 4.4 with NaOH 5 N. The titer of the solution was found to be 350.89 mg/ml.

Figure 2:
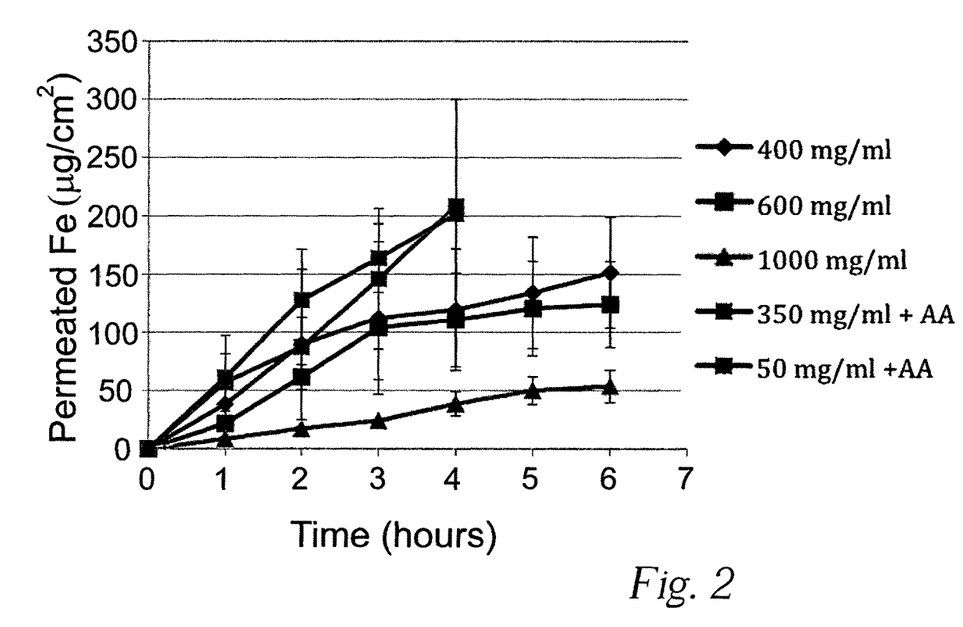
FIG. 2 shows permeation charts of solutions of Fe++ ascorbate with and without ascorbic acid obtained in the Franz cell. The vertical axis plots the permeated divalent Fe (in micrograms per square centimeter of membrane), while the horizontal axis plots time (in hours).

These solutions, subjected to absorption tests by means of diffusion cells according to example 1, yielded the data given in FIG. 2.

EXAMPLE 3

The complex of FeOOH with a maltodextrin (Fe$^{+++}$-polymaltose with molecular weight of 300,000 Da), measured in the Franz cell as in example 1, was used as Fe$^{+++}$. 4 g of powder were suspended in 10 ml of physiological solution. The suspension was left under magnetic agitation for 15 hours, at the end of which it was filtered with regenerated cellulose filters (pore diameter 0.45 µm). The Fe$^{+++}$ polymaltose concentration that corresponded to solubility was found to be 270.23±14.47 mg/ml. By using the experimental design according to example 1, the ferric polymaltose yielded no level of permeation, demonstrating that despite its solubility it is not bioavailable if administered through the sublingual pathway.

EXAMPLE 4

Figure 3:
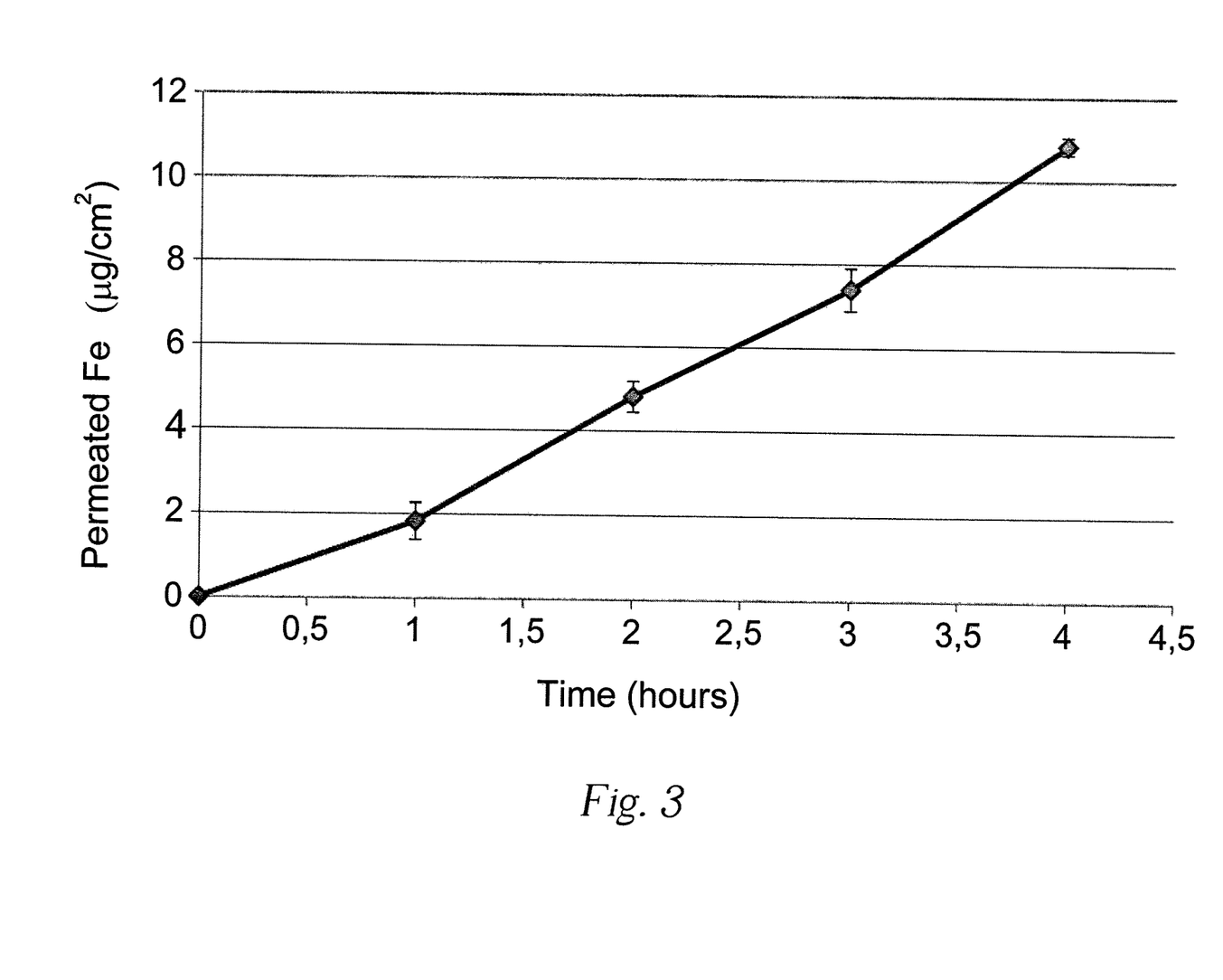

Another compound of Fe$^{+++}$ used in the absorption tests as in example 1 was ferric citrate. An excess of powder was suspended in 10 ml of physiological solution. The suspension was left under magnetic agitation for 15 hours, at the end of which it was filtered with regenerated cellulose filters (pore diameter 0.45 µm). The concentration of Fe$^{+++}$ citrate that corresponded to solubility was found to be 280 mg/ml. The pH of the solution was 1.2. The absorption chart is shown in FIG. 3.

Fe+++ absorption occurs exclusively at pH values lower than 2; at higher pH values, Fe+++ is no longer available because it precipitates.

EXAMPLE 5

Sublingual Tablets:

36.35 kg of iron ascorbate (equal to 5 kg of Fe++), 60.00 kg of maltodextrin, 20.00 kg of ascorbic acid are added in a conical mixer. After 15 minutes of mixing, 1.50 kg of magnesium stearate, 25.00 kg of polyvinylpyrrolidone and 3.00 kg of lemon fragrance are added in sequence. After another 15 minutes of mixing, the powder is compressed with a cambered punch with a diameter of 7.0 mm, obtaining tablets with an average weight of 145.85 mg (equal to 5 mg of Fe++ per tablet).

Sublingual Powder:

36.35 kg of iron ascorbate (equal to 5 kg of Fe++), 60.00 kg of maltodextrin, 20.00 kg of ascorbic acid are added in a conical mixer. After 15 minutes of mixing, 47.39 kg of fructose and 3.00 kg of lemon fragrance are added in sequence. After another 15 minutes of mixing, the powder is divided into sachets containing 40.75 mg (equal to 5 mg of Fe++ per sachet).

EXAMPLE 6

Alternative Sublingual Powder (Content of 1 Sachet with Powder Mix):

Fe(II) ascorbate 40 mg (equal to 5 mg of $Fe^{++}$); fructose 60 mg; ascorbic acid 10 mg; lemon fragrance 5 mg.

EXAMPLE 7

Sublingual Administration of 30 mg of Fe2+ as Fe2+ Ascorbate.

In order to explore in vivo bioavailability of the new compositions according to the present disclosure, a randomized clinical study was conducted in healthy volunteer patients (n=2), to whom a daily dose of 30 mg of Fe2+ was administered in the form of the compositions described here (6 sachets containing 40 mg of Fe2+ ascorbate according to example 6 cited above).

More particularly, the patients participating in the clinical study (healthy male volunteers; age 18-55 years; body mass index between 18.5 and 30 $kg/m^2$) were administered while fasting a quantity of 30 mg of Fe2+ in sublingual formulation, divided into six sachets, taken immediately one after the other with the indication to avoid swallowing the formulation and/or saliva for at least 4 minutes.

The participants were hospitalized for two days prior to administration until the next day and were under medical observation.

Blood samples were taken 24 and 22 hours prior to administration as well as upon administration (time 0.0) and subsequently at times 0.033 (2 minutes), 0.10 (6 minutes); 0.20 (12 minutes); 0.33 (20 minutes); 0.50 (30 minutes); 0.75 (45 minutes); 1.00 (60 minutes); 1.25 (1 hour 15 minutes); 1.50 (1 hour 30 minutes); 1.75 (1 hour 45 minutes) and 2.00 (2 hours).

The samples were then analyzed with respect to the trend of (average) concentrations of various indicators over time.

Detected values:
Total iron measured in micrograms/dl (ICP-MS)
Free iron by ultrafiltration measured in micromoles/liter (=NTBI) (ICP-MS)
Total iron binding capacity (TIBC) measured in micrograms/dl (column separation, Vitros analyzer)
Transferrin saturation (PTS) measured in %
Serum iron (SI), measured in micrograms/dl, colorimetric method (Vitros analyzer)
Results:
Development of Serum Iron Over Time:

| Time | Serum Fe (μg/dl) |
| --- | --- |
| 0 | 0 |
| 0.033 | 5.5 |
| 0.100 | 7 |
| 0.200 | 6 |
| 0.330 | 10 |
| 0.500 | 24 |
| 0.750 | 51.5 |
| 1.000 | 72 |
| 1.250 | 91 |
| 1.500 | 110.5 |
| 1.750 | 118.5 |
| 2.000 | 129 |

Development of Total Iron Over Time

| Time | Total iron (μg/dl) |
| --- | --- |
| 0.00 | 0 |
| 0.03 | −7.4 |
| 0.10 | 6.2 |
| 0.20 | −13.54 |
| 0.33 | 5.95 |
| 0.50 | 6.37 |
| 0.75 | 41.58 |
| 1.00 | 51.01 |
| 1.25 | 80.17 |
| 1.50 | 90.15 |
| 1.75 | 95.7 |
| 2.00 | 110.94 |

Development of Total Iron Binding Capacity Over Time:

| Time | TIBC(μg/dl) |
| --- | --- |
| 0.000 | 0 |
| 0.033 | −30.5 |
| 0.100 | −22 |
| 0.200 | −25 |
| 0.330 | −1 |
| 0.500 | −52.5 |
| 0.750 | −21.5 |
| 1.000 | −46.5 |
| 1.250 | −20.5 |
| 1.500 | −42.5 |
| 1.750 | −28 |
| 2.000 | −44.5 |

Development of Transferrin Saturation and Free Iron Over Time:

| Time (min) | Transferrin saturation (%) | NTBI (μM/l) |
| --- | --- | --- |
| 0 | 24 | 0.000 |
| 2 | 28 | −0.306 |
| 6 | 28 | −0.215 |
| 12 | 28.5 | 0.029 |
| 20 | 26.5 | 0.067 |
| 30 | 36 | 0.106 |
| 45 | 40.5 | 0.448 |
| 60 | 50 | 0.311 |
| 75 | 51.5 | 1.191 |
| 90 | 60 | 0.084 |
| 105 | 49.5 | 0.806 |
| 120 | 66.5 | 0.339 |

Figure 4:
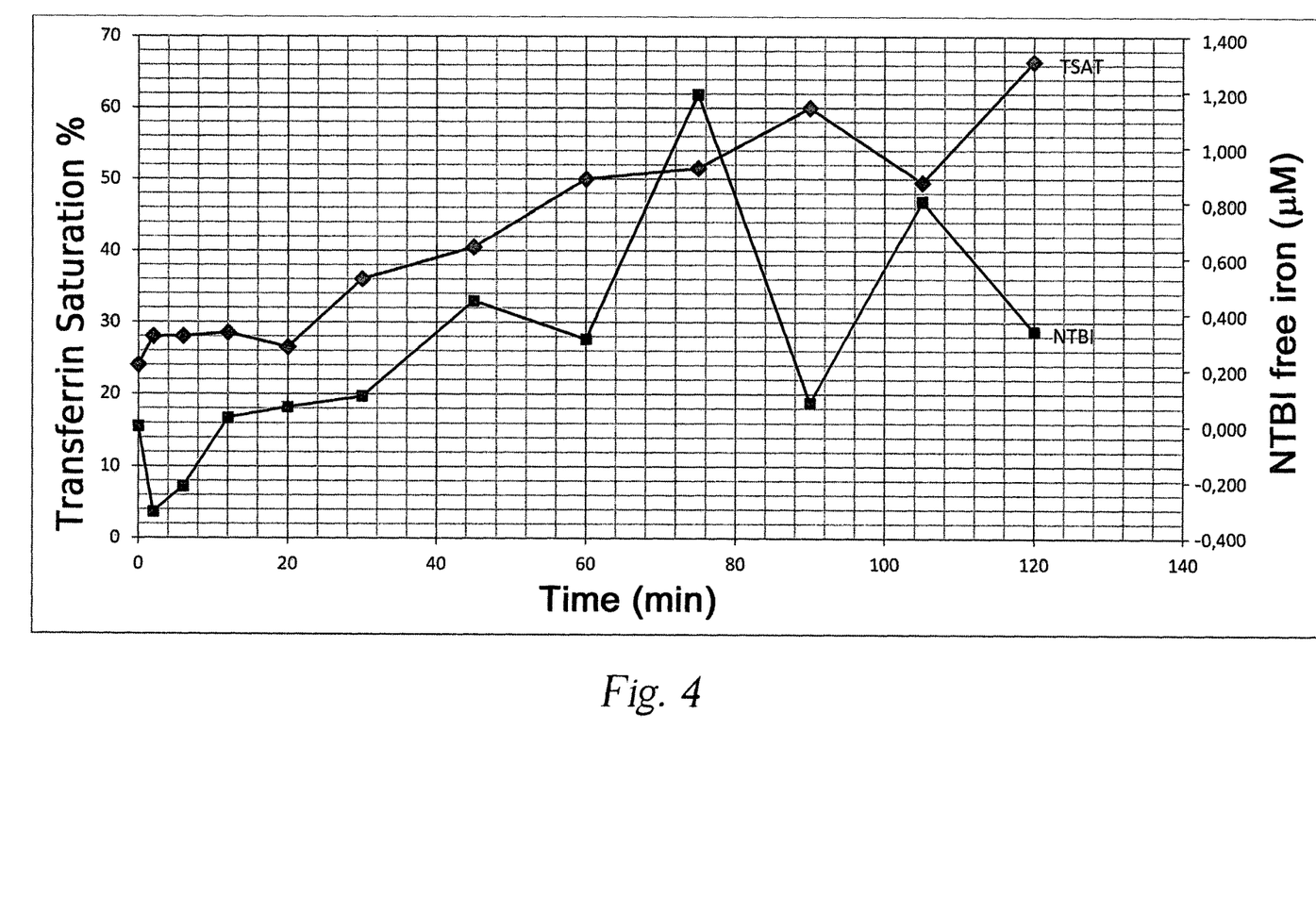
FIG. 4 shows the saturation of transferrin (as a percentage, on the vertical axis on the left) and free non transferrin bound iron (NTBI) (in micromoles/liter on the vertical axis on the right) over time (minutes) after sublingual administration of 30 mg of divalent Fe according to the present disclosure.

The results presented in the last table as above are shown graphically in FIG. 4, where the horizontal axis plots time while the vertical axis on the left plots NTBI and the vertical axis on the right plots saturation.

The table shown above and FIG. 4 show that after the administration of 30 mg of Fe2+ (as ascorbate) through the sublingual pathway as described by the present disclosure, the increase in transferrin saturation (PTS, approximately at 24% at the time of administration) after 2 hours reaches 42.5% (65.5% absolute saturation), while the free iron (NTBI) passes from 0 to 0.34 micromoles/liter.

Figure 5:
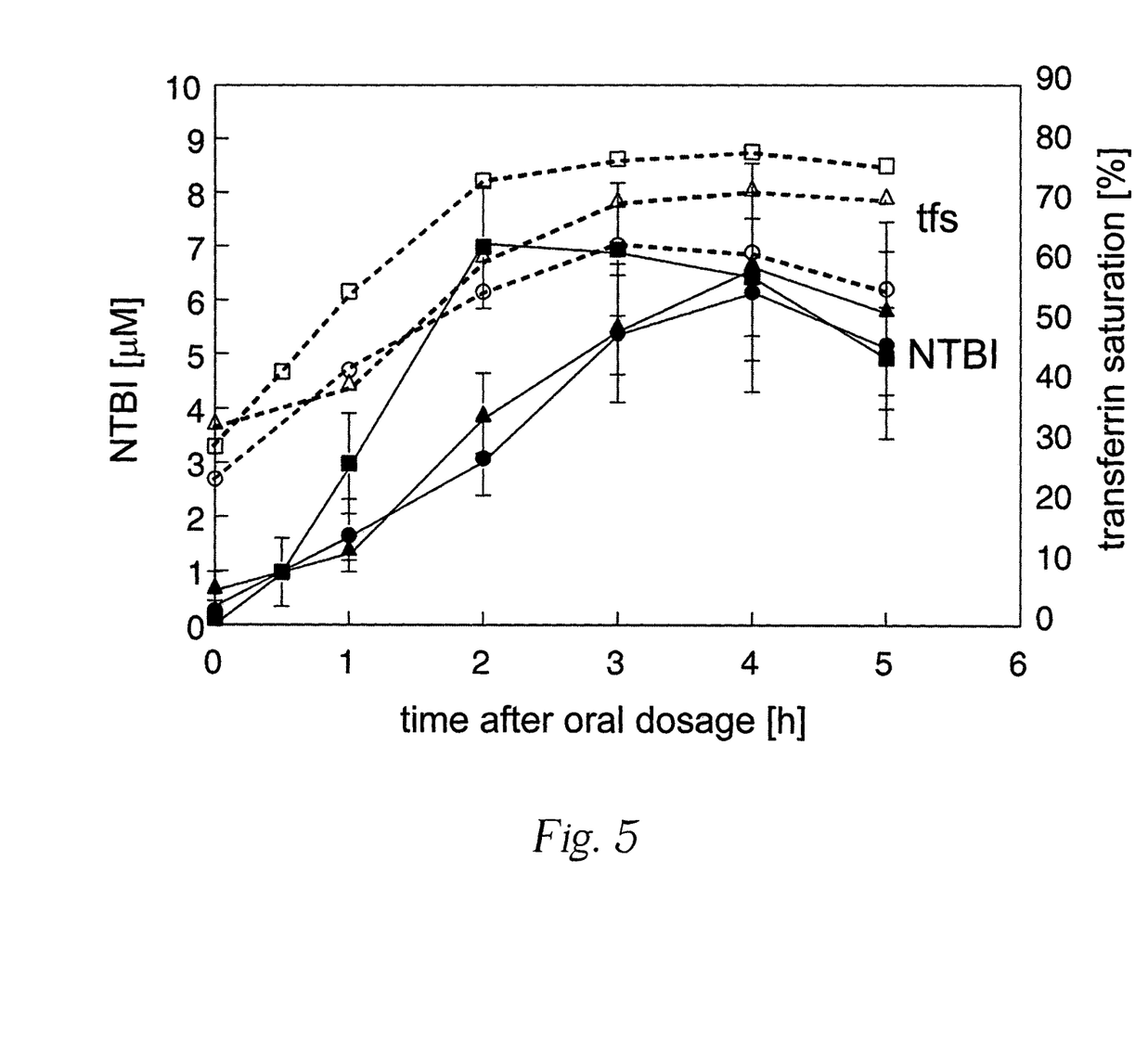
FIG. 5 plots transferrin saturation (as a percentage, on the vertical axis on the right) and free non-transferrin bound iron (NTBI) in micromoles/liter on the vertical axis on the left) over time (hours) after oral (gastrointestinal) administration of 100 mg of divalent Fe according to Dresow et al., Biometals (2008), 21, 273-276.

Vice versa, as shown in FIG. 1 of Dresow et al., Biometals (2008), 21, 273-276 as reproduced in FIG. 5, the classic oral administration of 100 mg of Fe2+ (as ascorbate) orally to healthy volunteers leads to an increase in transferrin saturation after 2 hours of approximately 45% (i.e. from approximately 30% at the time of administration followed by approximately 75% absolute saturation after two hours— see white squares), while free iron (NTBI) passes within the same two hours from 0 to 6.7 micromoles/liter—see black squares.

Comparison of the results obtained with the formulations and the doses according to the present disclosure with data recently published in the literature (Dresow et al.) therefore highlights the particular effectiveness of sublingual administration with respect to classic oral (gastrointestinal) therapy, especially in view of reaching a good degree of transferrin saturation after administration of a relatively modest dose (30 mg of Fe2+ per day are a little under one third of the classic oral daily dose of 100 mg of divalent Fe) correlated at the same time with a low index of free iron ("NTBI", non-transferrin bound iron), which is instead the highest risk factor associated with iron administration.

Intrabuccal administration, preferably sublingual administration, of Fe2+ according to the present disclosure therefore allows to saturate transferrin, using reduced doses (with respect to classic oral administration), achieving an equal effectiveness of saturation accompanied at the same time by a conspicuous reduction in the correlated risk, thus improving significantly the risk/benefit ratio of the administration of divalent iron compared with its classic oral (gastrointestinal) administration.

Preferred Embodiments Of The Present Disclosure

In view of the teachings of the preceding chapters, some preferred but not exclusive embodiments of the present disclosure are described hereinafter:

First Embodiment:

A divalent iron compound for use in hyposideremia therapy by administration through intrabuccal absorption, preferably through sublingual absorption in a patient, said use providing for the administration of divalent iron at doses comprised in an interval from 1 to 90 mg of divalent Fe per day for a human patient, preferably 1 to 60 mg of divalent Fe per day for a human patient, more preferably 4 to 40 mg of divalent Fe per day for a human patient, even more preferably 5 to 30 mg of divalent Fe per day for a human patient, to reduce, for an equal increment in transferrin saturation, the onset of free non transferrin bound iron with respect to gastrointestinal administration.

Second Embodiment:

A divalent iron compound, preferably according to the first embodiment, for use in the therapy of iron malabsorption due to celiac disease or chronic inflammatory bowel diseases by administration through intrabuccal absorption, preferably through sublingual absorption in a patient, said use providing for the administration of divalent iron at doses comprised in an interval from 10 to 90 mg of divalent Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient.

Third Embodiment:

A divalent iron compound according to the second embodiment, for use in the therapy of iron malabsorption due to celiac disease or chronic inflammatory bowel diseases by administration through intrabuccal absorption, preferably through sublingual absorption in a patient, said use providing for the administration of divalent iron at doses comprised in an interval from 45 to 65 mg of divalent Fe per day for a human patient.

Fourth Embodiment:

A divalent iron compound, preferably according to the first embodiment, for use in therapy of chronic sideropenic anemia caused by blood losses by administration through intrabuccal absorption, preferably through sublingual absorption in a patient, said use providing for the administration of divalent iron at doses comprised in an interval from 10 to 90 mg of divalent Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient.

Fifth Embodiment:

A divalent iron compound according to the fourth embodiment, for use in therapy of chronic sideropenic anemia caused by blood losses by administration through intrabuccal absorption, preferably through sublingual absorption in a patient, said use providing for the administration of divalent iron at doses comprised in an interval from 45 to 65 mg of divalent Fe per day for a human patient.

Sixth Embodiment:

A divalent iron compound for use in therapy of relapsing anemic states treated previously with gastrointestinal therapy using divalent or trivalent iron compounds, or treated previously with parenteral therapy using trivalent iron compounds, said use providing for administration through intrabuccal absorption, preferably through sublingual absorption of the divalent iron compound to the patient in order to reduce, for an equal increment in transferrin saturation, the onset of free non transferrin bound iron with respect to gastrointestinal administration.

Seventh Embodiment:

A divalent iron compound according to the sixth embodiment, for use in therapy of relapsing anemic states treated previously with gastrointestinal therapy using divalent or trivalent iron compounds or treated previously with parenteral therapy using trivalent iron compounds, said use providing for administration through intrabuccal absorption, preferably through sublingual absorption to the patient of divalent iron at doses comprised in an interval from 1 to 90 mg of divalent Fe per day for a human patient, preferably 1 to 60 mg of divalent Fe per day for a human patient, more preferably 4 to 40 mg of divalent Fe per day for a human patient, even more preferably 5 to 30 mg of divalent Fe per day for a human patient.

Eighth Embodiment:

A divalent iron compound, preferably according to the seventh embodiment, for use in therapy of relapsing anemic states due to chronic sideropenic anemia caused by blood losses or of relapsing anemic states caused by iron malabsorption due to celiac disease or chronic inflammatory bowel diseases and treated previously with gastrointestinal therapy using divalent or trivalent iron compounds or treated previously with parenteral therapy using trivalent iron compounds, said use providing for administration through intrabuccal absorption, preferably through sublingual absorption to the patient of divalent iron at doses comprised in an interval from 10 to 90 mg of divalent .Fe per day for a human patient, preferably 30 to 90 mg of divalent Fe per day for a human patient, more preferably 40 to 90 mg of divalent Fe per day for a human patient, even more preferably 45 to 90 mg of divalent Fe per day for a human patient.

Ninth Embodiment:

A divalent iron compound according to the eighth embodiment, for use in therapy of relapsing anemic states due to chronic sideropenic anemia caused by blood losses or of relapsing anemic states caused by iron malabsorption due to celiac disease or chronic inflammatory bowel diseases and treated previously with gastrointestinal therapy using divalent or trivalent iron compounds or treated previously with parenteral therapy using trivalent iron compounds, said use providing for administration through intrabuccal absorption, preferably through sublingual absorption to the patient of divalent iron at doses comprised in an interval from 45 to 65 mg of divalent Fe per day for a human patient.

Tenth Embodiment:

A divalent iron compound according to one or more of the first to ninth embodiments, its use providing for a therapeutic regimen of 1-6, preferably 1-3 single administrations per day to yield the daily doses according to the first embodiment to the ninth embodiment.

Eleventh Embodiment:

A divalent iron compound according to one or more of the first to tenth embodiments, for use according to one or more of the first to tenth embodiments, the administration of which occurs through sublingual absorption.

Twelfth Embodiment:

A divalent iron compound according to the eleventh embodiment, for use according to one or more of the first to eleventh embodiments, wherein administration occurs with the indication to the patient to avoid swallowing the formulation that contains the divalent iron compound and/or saliva for a period of time of at least 30 seconds, preferably at least one minute, more preferably at least two minutes, even more preferably at least four minutes after placing the formulation containing the divalent iron compound in the intrabuccal cavity, preferably under the tongue.

Thirteenth Embodiment:

A divalent iron formulation with intrabuccal absorption, preferably with sublingual absorption, prepared in single doses comprised in an interval from 0.5 to 30 mg of divalent Fe, preferably 3 to 20 mg of divalent Fe, more preferably 3 to 10 mg of divalent Fe for use in hyposideremia therapy in a patient, in order to reduce, for an equal increment in transferrin saturation, the onset of free non transferrin bound iron with respect to gastrointestinal administration.

Fourteenth Embodiment:

A divalent iron formulation according to the thirteenth embodiment, for use in therapy of iron malabsorption due to celiac disease or chronic inflammatory bowel diseases, of chronic sideropenic anemia due to blood losses or of relapsing anemic states treated previously with gastrointestinal therapy with divalent or trivalent iron compounds or treated previously with parenteral therapy using trivalent iron compounds.

Fifteenth Embodiment:

A formulation according to the thirteenth or fourteenth embodiment, in a form of administration selected from the group constituted by intrabuccal tablets, sublingual tablets, oral drug strips (i.e., intrabuccal or sublingual films), wafers (i.e., intrabuccal or sublingual flat elements), granulated or powdered material, sprays, foams, gels or intrabuccal paste.

Sixteenth Embodiment:

A formulation according to the fifteenth embodiment, wherein the intrabuccal tablets, sublingual tablets, oral drug strips (i.e., intrabuccal or sublingual films) or wafers (i.e., intrabuccal or sublingual flat elements) have a film-like shape, in particular have a total thickness from 0.05 to 3 mm, preferably 0.1 to 1 mm, even more preferably 0.1 to 0.5 mm, and an area of preferably 0.5 to 20 cm2, preferably 1 to 10 cm2.

Seventeenth Embodiment:

A formulation according to the thirteenth to sixteenth embodiments, with sublingual absorption.

Eighteenth Embodiment:

A formulation according to one or more of the thirteenth to seventeenth embodiment, for use in hyposideremia therapy by administration through intrabuccal absorption, preferably through sublingual absorption in a patient, said use providing for the administration of divalent iron at doses comprised in an interval between 1 and 90 mg of divalent Fe per day for a human patient, preferably 1 to 60 mg of divalent Fe per day for a human patient, more preferably 4 to 40 mg of divalent Fe per day for a human patient, even more preferably 5 to 30 mg of divalent Fe per day for a human patient.

Nineteenth Embodiment:

A divalent iron formulation according to one or more of the thirteenth to eighteenth embodiments, or a divalent iron compound according to one or more of the first to twelfth embodiments, wherein the divalent iron compound is constituted by a salt or complex of divalent iron, soluble at pH values that are pharmaceutically acceptable for administration through intrabuccal absorption.

Twentieth Embodiment:

A formulation or compound according to the nineteenth embodiment, wherein the divalent iron compound is selected from the group that consists of ferrous sulfate, ferrous citrate, ferrous ascorbate, ferrous fumarate, ferrous glycinate and ferrous gluconate, the compound being preferably ferrous ascorbate.

Twenty-first Embodiment:

A formulation according to one or more of the thirteenth to twentieth embodiments, comprising buffering and/or reducing excipients, preferably ascorbic acid/ascorbate, in an amount adapted to obtain a pH between 2.0 and 6.5, preferably between 2.5 and 4.5 in the oral cavity of the patient.

Twenty-second Embodiment:

A formulation according to one or more of the thirteenth to twenty-first embodiments, comprising at least one polymeric phase that constitutes 10-90% (w/w), preferably 20-70% (w/w), more preferably 20-50% (w/w) of the entire formulation.

Twenty-third Embodiment:

A formulation according to one or more of the thirteenth to twenty-second embodiments, characterized in that it is mucoadhesive or exhibits at least one mucoadhesive surface.

Twenty-fourth Embodiment:

A solid formulation according to one or more of the thirteenth to twenty-third embodiments, characterized in that it breaks down rapidly in aqueous environments, preferably in saliva, preferably within 10 seconds to 5 minutes, more preferably within 30 seconds to 3 minutes, even more preferably within 1 minute to 2 minutes, releasing the entire divalent iron compound.

Twenty-fifth Embodiment:

A formulation according to one or more of the thirteenth to twenty-fourth embodiments, characterized in that the formulation comprises an additional active ingredient, for example folic acid.

The disclosures in Italian Patent Application no. MI2013A001147, from which this application claims priority, are incorporated herein by reference.

Where technical features mentioned in any claim are followed by reference signs, those reference signs have been included for the sole purpose of increasing the intelligibility of the claims and accordingly such reference signs do not have any limiting effect on the interpretation of each element identified by way of example by such reference signs.

The invention claimed is:

1. A method of treating hyposideremia in a patient, said method comprising administering a divalent iron compound through sublingual absorption in a patient, wherein said administration occurs with indication to the patient to avoid swallowing the formulation containing the divalent iron compound and/or saliva for a period of at least 30 seconds after placement of the formulation containing the divalent iron compound in the sublingual cavity, said method providing for the administration of divalent iron at doses comprised in an interval from 1 to 90 mg of divalent Fe per day for a human patient,
wherein the divalent iron compound is selected from the group consisting of ferrous citrate and ferrous ascorbate.

2. The method according to claim 1, which method is employed (i) in the therapy of iron malabsorption due to celiac disease or chronic inflammatory bowel diseases or (ii) in the therapy of chronic sideropenic anemia caused by blood losses or (iii) in the therapy of relapsing anemic states caused by chronic sideropenic anemia caused by blood losses or of relapsing anemic states caused by iron malabsorption due to celiac disease or chronic inflammatory bowel diseases, said relapsing anemic states having been treated previously with gastrointestinal therapy using divalent or trivalent iron compounds or treated previously with parenteral therapy using trivalent iron compounds, which method is carried out by administration through sublingual absorption in a patient, said method providing for the administration of divalent iron at doses comprised in an interval from 30 to 90 mg of divalent Fe per day for a human patient.

3. The method according to claim 2, said method providing for the administration of divalent iron at doses comprised in an interval from 45 to 65 mg of divalent Fe per day for a human patient.

4. The method according to claim 2, said method providing for a therapeutic regimen of 1-6 single administrations per day to yield the daily doses.

5. The method according to claim 4, wherein the therapeutic regimen is of 1-3 single administrations per day.

6. The method according to claim 1, to be applied in the therapy of relapsing anemic states, said relapsing anemic states having been treated previously with gastrointestinal therapy using divalent or trivalent iron compounds or treated previously with parenteral therapy using trivalent iron compounds.

7. The method according to claim 1, wherein the compound is ferrous citrate.

8. A method of treating hyposideremia in a patient, said method comprising administering a divalent iron compound is constituted by a salt or complex of divalent iron, soluble at pH values that are pharmaceutically acceptable for administration through sublingual absorption, said formulation being prepared in single doses in an interval from 0.5 to 30 mg of divalent Fe, in which method administration occurs with indication to the patient to avoid swallowing the formulation containing the divalent iron compound and/or saliva for a period of time of at least 30 seconds after placement of the formulation containing the divalent iron compound in the sublingual cavity, wherein the divalent iron compound is selected from the group consisting of ferrous citrate and ferrous ascorbate.

9. The method according to claim 8, wherein the compound is ferrous ascorbate.

10. The method according to claim 8, wherein the form of administration is selected from the group consisting of sublingual tablets, oral drug strips, wafers, granulated or powdered material, sprays, foams, and gels or sublingual paste.

11. The method according to claim 8, wherein the formulation comprises buffering and/or reducing excipients in an amount adapted to obtain a pH between 2.0 and 6.5 in the oral cavity of the patient.

12. The method according to claim 11, wherein the formulation comprises buffering and/or reducing excipients in an amount adapted to obtain a pH between 2.5 and 4.5 in the oral cavity of the patient.

13. The method according to claim 8, wherein the formulation comprises an additional active ingredient.

14. The method according to claim 13, wherein the additional active ingredient is folic acid.

15. The method according to claim 8, wherein the compound is ferrous citrate.

16. A method of treating hyposideremia in a patient, said method comprising administering a divalent iron formulation through sublingual absorption, wherein the divalent iron compound is the sole active ingredient within said formulation and is constituted by ferrous citrate, soluble at pH values that are pharmaceutically acceptable for administration through sublingual absorption, said formulation being a powdered material prepared in single doses in an interval from 0.5 to 30 mg of divalent Fe, in which method administration occurs with indication to the patient to avoid swallowing the formulation containing the ferrous citrate and/or saliva for a period of time of at least 30 seconds after placement of the formulation containing the divalent iron compound in the sublingual cavity.

17. The method according to claim 16, wherein the formulation comprises buffering and/or reducing excipients in an amount adapted to obtain a pH between 2.0 and 6.5 in the oral cavity of the patient.

18. The method according to claim 17, wherein the formulation comprises buffering and/or reducing excipients in an amount adapted to obtain a pH between 2.5 and 4.5 in the oral cavity of the patient.

19. The method according to claim 16, to be applied in the therapy of relapsing anemic states, said relapsing anemic states having been treated previously with gastrointestinal therapy using divalent or trivalent iron compounds or treated previously with parenteral therapy using trivalent iron compounds.

* * * * *